Figure 1:
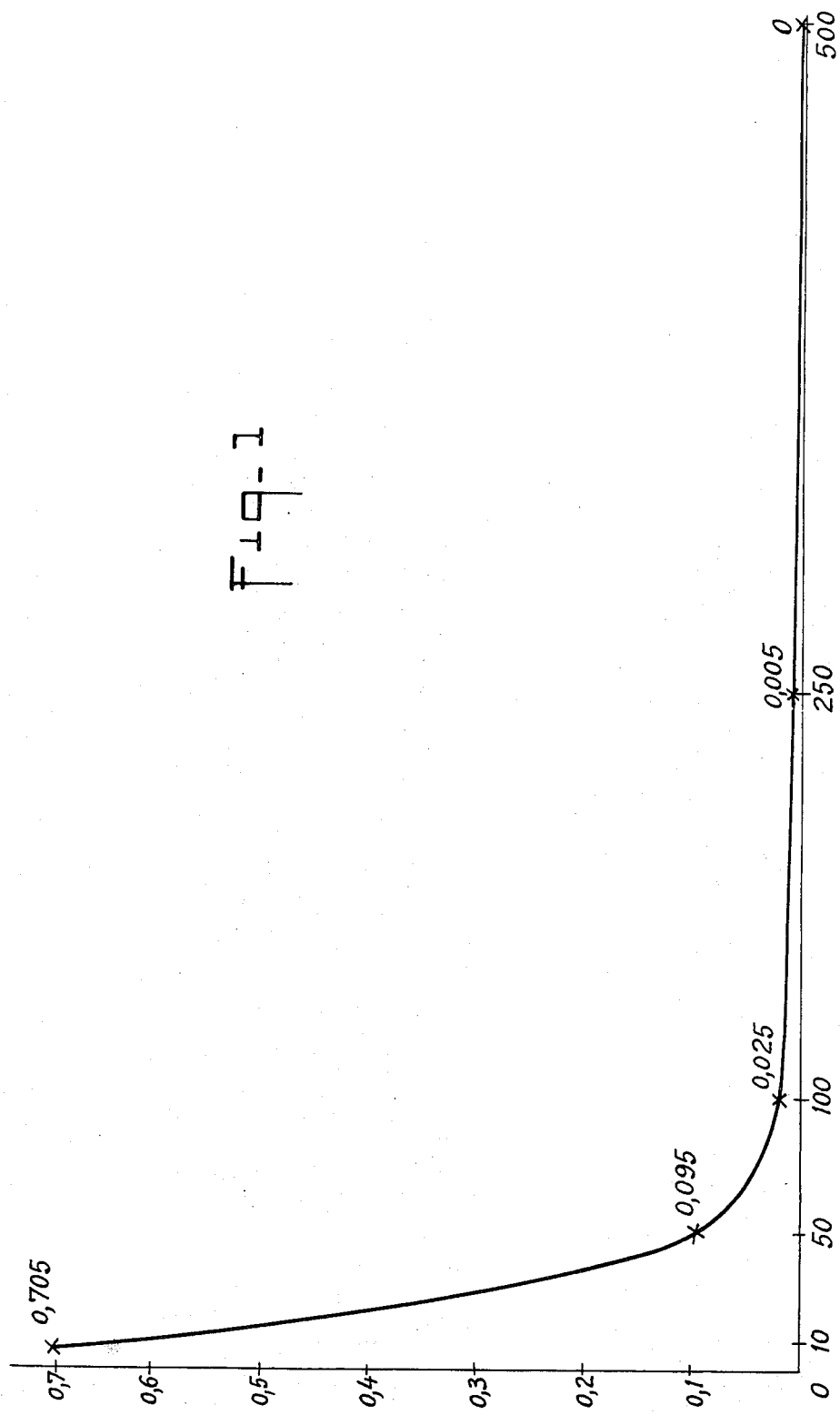

United States Patent [19]

Truffier et al.

[11] 4,112,074

[45] Sep. 5, 1978

[54] COMPOSITIONS COMPRISING OVOMUCOID FRACTION OF WHITE OF QUAIL'S EGG

[76] Inventors: Jean-Claude Truffier, 67 rue Thiers, 17300 Rochefort; Gérard Lucotte, 69 avenue F. Mollet, 92160 Antony; Raymond Cordonnier, Le Vergeroux, 17300 Rochefort, all of France

[21] Appl. No.: 810,638

[22] Filed: Jun. 27, 1977

[30] Foreign Application Priority Data

Jun. 29, 1976 [FR] France .................................. 76 19751

[51] Int. Cl.$^2$ ...................... A61K 37/02; A61K 35/54
[52] U.S. Cl. ...................................... 424/177; 424/105
[58] Field of Search ................................ 424/105, 177

[56] References Cited

PUBLICATIONS

Koga et al – Chem. Abst., vol. 81 (1974), p. 131, 808q.
Koga et al – Chem. Abst., vol. 72 (1970), p. 197f.

*Primary Examiner*—Sam Rosen

[57] ABSTRACT

The invention concerns a ovomucoid fraction which has been isolated from quail eggs, particularly of the sub-species Coturnix coturnix, japonica, characterized by its beef antitrypsine activity (100 units of antitrypsin per mg) and by the fact that it consists primarily of a postalbumin and protein which corresponds to protein as evidenced by the proteinogram obtained by electrophoretitics on gelatinized starch.

This ovomucoid fraction is a medication useful for the treatment of numerous allergies, and it acts not so much as an antihistamine but rather acts as modifying the surface.

4 Claims, 4 Drawing Figures

COMPOSITIONS COMPRISING OVOMUCOID FRACTION OF WHITE OF QUAIL'S EGG

The present invention relates to the isolation, from the white of quail's eggs, and to the purification, of an ovomucoid fraction characterized by its antiprotease activity and in particular its antitrypsin activity, and to the application of this purified ovomucoid fraction as a medicament which is in particular useful for the treatment of various types of allergy.

The white of quail's eggs exhibits an antiprotease activity, and this activity is concentrated in the ovomucoid fraction of the white of egg. The ovomucoid fraction of the white of quail's eggs isolated in accordance with the invention is characterized by its activity towards cattle trypsin.

The study has been carried out principally on the eggs of a sub-species of quail called Coturnix coturnix japonica and, more precisely, of strain A of this sub-species raised at 1a Tublerie by R. Cordonnier.

The anti-protease activity of the white of egg was measured by the conventional azocoll method (azo dyestuff in suspension in collagen). This reagent serves both as a dyestuff and as a substrate, and the coloration of the peptides liberated by the action of the proteases on the collagen is measured. The activity of a protease (such as trypsin or chymotrypsin) is measured as follows:

In each of the 5 test tubes, 15 mg of azocoll are diluted in 1 cm$^3$ of tris-HCl buffer of pH = 7.5, to which calcium chloride ($2 \times 10^{-3}$ M) and $\beta$-mercapto-ethanol (1 millimole) are added. To each tube, 10, 20, 30, 50 and 100 $\gamma$ of protease are added respectively. The color reactions are measured simultaneously after 5 minutes' continuous stirring at 37° C.; the optical density at 580 nm of the solutions is determined after centrifuging, on a sample of 0.8 cm$^3$ of supernatant liquor. The protease activity is expressed by the variation in the optical density ($D_0$) per minute and per mg of protease.

To measure the anti-protease activity of the white of egg, the same procedure is followed but increasing amounts of white of egg are added to the tubes containing a constant amount of protease. The activity of the white of egg towards cattle trypsin and cattle $\alpha$-chymotrypsin was measured. The anti-trypsin activity of the white of quail's eggs being very high, the determinations of the anti-trypsin activity were carried out using white of egg diluted 1/10, and measuring the coloration obtained at 37° C., after 5 minutes, by the action of 100 $\Delta$g of trypsin together with samples of 10, 50, 100, 250 and 500 $\gamma$ of diluted white of egg. The results are shown in FIG. 1 by a curve plotted with the optical densities as ordinates and the weight in $\gamma$ of white of egg diluted 1/10 as the abscissae.

Figure 2:
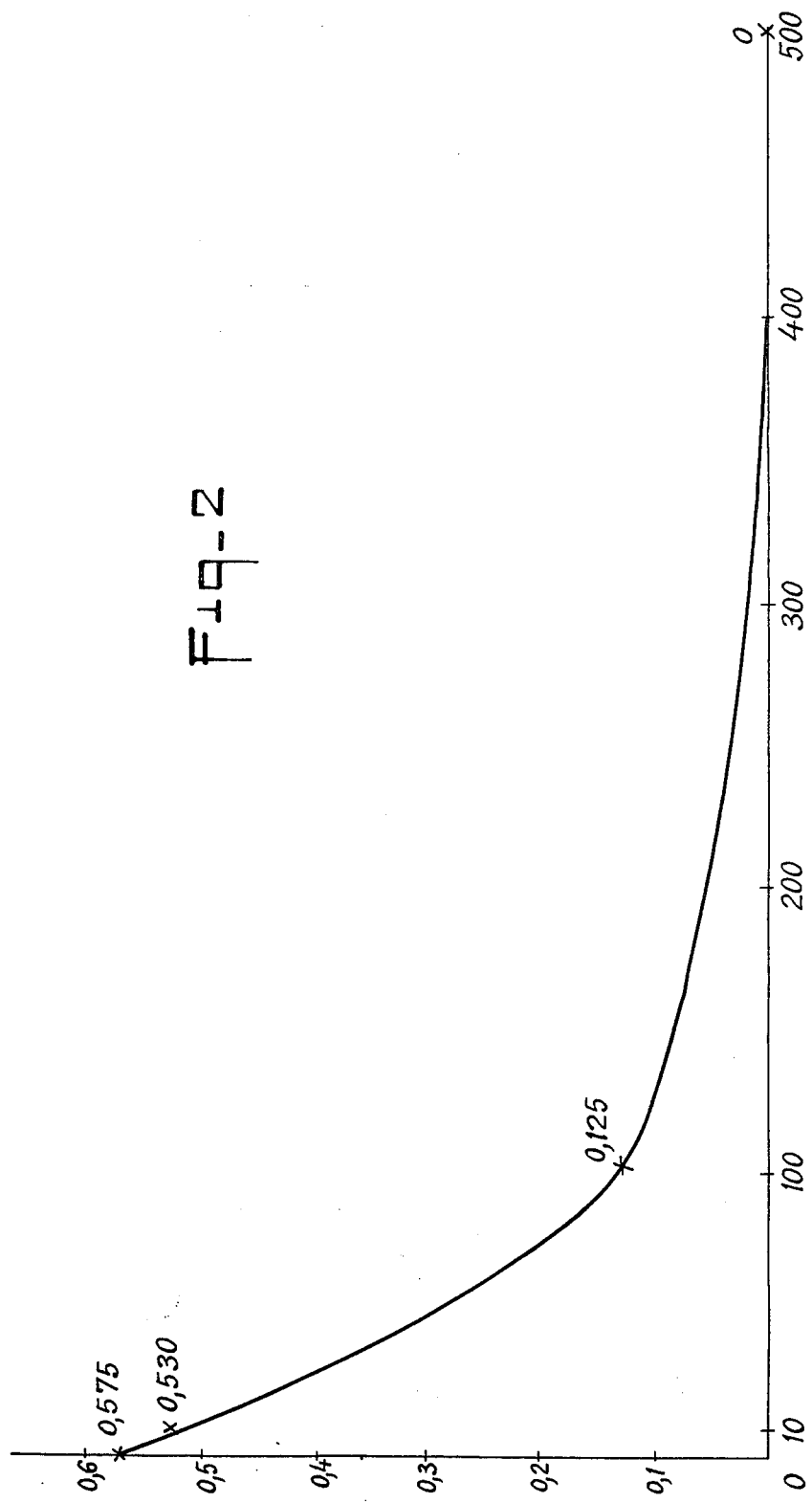

The activity of the white of egg towards $\alpha$-chymotrypsin was determined in the same manner, but is much less than towards trypsin. The results of the measurements carried out using 1 mg of $\alpha$-chymotrypsin and samples of 10, 100 and 500 $\gamma$ of undiluted white of egg are shown in FIG. 2, where the optical densities have been plotted as ordinates and the weight in $\gamma$ of white of egg as abscissae.

The invention relates to a process for isolating, from quails eggs, an ovomucoid fraction having an increased anti-trypsin activity; the invention also relates to the product thus obtained and to its application as a medicament.

The process according to the invention results from an adaptation of the conventional processes of isolating ovomucoid.

The whites of egg used came from the breeding establishment of R. Cordonnier, the high performance reproducing strain from which appears to be characterized by a large amount of the albumin. In all cases, the samples were taken, preceding migration, from fresh eggs (laid in the same week). The whites of eggs were stored in small Plexiglas tubes which were sterilized and closed with plastic stoppers. They can be kept for several months in a cold room at 4° C. without any change in the proteinogram. However it is necessary to avoid prolonged storage in a refrigerator, and above all to avoid successive freezings and thawings.

The process of isolating and purifying the active fraction is as follows:

The white of egg (250 cm$^3$) is brought to pH 3.5 by slow addition of one volume of a trichloroacetic acid-/acetone solution (1 volume of 0.5 M trichloroacetic acid + 2 volumes of acetone), whilst slowly revolving a glass rod in the crystallizer which contains the white of egg. The resulting creamy liquid is placed in a settling ampoule for 48 hours at +4° C. The supernatant liquor must be clear and the settling or filtration must be repeated until this result is achieved; to do this, the supernatant liquid or filtrate can be heated at 80° C. for 5 minutes and subsequently refiltered.

The fraction having an increased anti-trypsin activity precipitates on addition of 2 to 3 volumes of acetone to the filtrate; this precipitation can be repeated several times and the precipitate either collected or filtered off. This precipitate, dissolved in water, is dialyzed to remove the excess trichloroacetic acid, reprecipitated, washed with acetone and ether and dried at room temperature.

In this way, about 1 mg of active product per 100 ml of white of egg is obtained. To preserve the maximum activity, it is preferable to avoid the stage of heating the supernatant liquid, though the anti-trypsin activity of the white of egg exhibits exceptional heat stability, as is shown by Table I below, which gives the percentage activity remaining after heating (at 100° C. and pH 6, and at 85° C. and pH 8.6) after varying times.

TABLE I

| minutes | % activity $\begin{cases} 100° C \\ pH = 6.0 \end{cases}$ | % activity $\begin{cases} 85° C \\ pH = 8.6 \end{cases}$ |
|---|---|---|
| 0 | 100 | 100 |
| 15 | 36 | 55 |
| 30 | 15 | 20 |
| 45 | 8 | 10 |
| 60 | 2 | 5 |

The anti-trypsin activity of the dry product thus obtained, which product is an object of the invention, was determined. The unit of anti-trypsin activity is defined by taking crystallized trypsin as the standard, and corresponds to the amount (in $\mu$g) of active product which, at 0° C. in a solution containing 50 $\mu$g of trypsin/ml in a borate buffer of pH 7.9, containing CaCl$_2$ ($10^{-2}$ M), reduces the speed of hydrolysis of the subtrate by 50%. Under these conditions, the product according to the invention contains, in the dry state, about 100 anti-trypsin units per mg.

Attempts have been made to identify the active fraction according to the invention by comparing the proteinograms of the entire white of egg and of the active fraction, obtained by electrophoresis on starch gel and by immunoelectrophoresis.

The preferred technique which has been employed to separate the proteins of the white of quail's eggs is horizontal electrophoresis on starch gel in a discontinuous system (tris-citrate buffer, pH 8.6), the proteins being developed with amide black. This technique has made it possible to mark the various proteins constituting the white of egg (G. Lucotte and M. Kaminski, Exp. Anim. 1, 21–41) on the proteinogram I reproduced in FIG. 3. ($a_1$, $a_2$ and $a_3$ are the pre-ovalbumins; $A_1$, $A_2$ and $A_3$ are the ovalbumins; pA is the post-ovalbumin; $G_2$ and $G_3$ are the ovoglobulins; $C_1$ and $C_2$ is the conalbumin; OM is the ovomacroglobulin; the proteins X and Y and L are the lysozyme).

Figure 3:
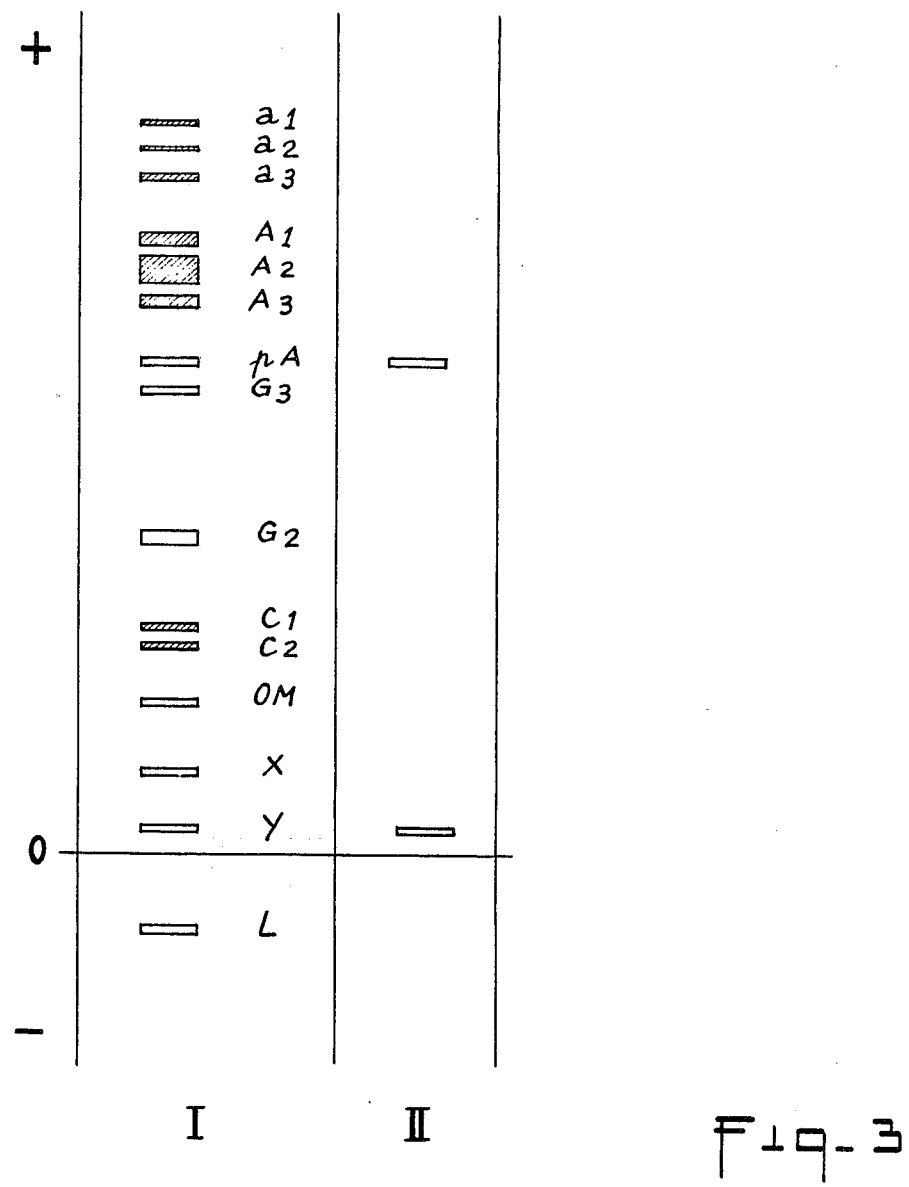

On analyzing, by the same electrophoretic method, the active fraction isolated according to the invention, a proteinogram II is obtained, which is also shown on FIG. 3, opposite that of the entire white of egg; it shows the presence of two proteins, one which migrates like the post-ovalbumin and is by virtue of this characteristic entirely comparable with bird ovomucoid (an inhibitor of normal proteases) whilst the second migrates like protein Y and tends to resemble the ovo-inhibitor (the inhibitor of prokaryotic proteases).

Furthermore, the white of egg, on the one hand, and the active fraction according to the invention, on the other, were analyzed by immunoelectrophoresis; anti-(white of egg) serum is obtained by immunizing rabbits with the white of egg; in the course of the immunoelectrophoresis, the proteins of the white of egg precipitate with the antibodies of the anti(white of egg) serum, in the form of arcs. The interpretation of these arcs or bands, of which the main ones are shown in FIG. 4, makes it possible to find once again the various proteins detected in the proteinogram obtained by electrophoresis, that is to say in particular the rings (1) = ovalbumin, (2) = postovalbumin and (3) = conalbumin.

Figure 4:
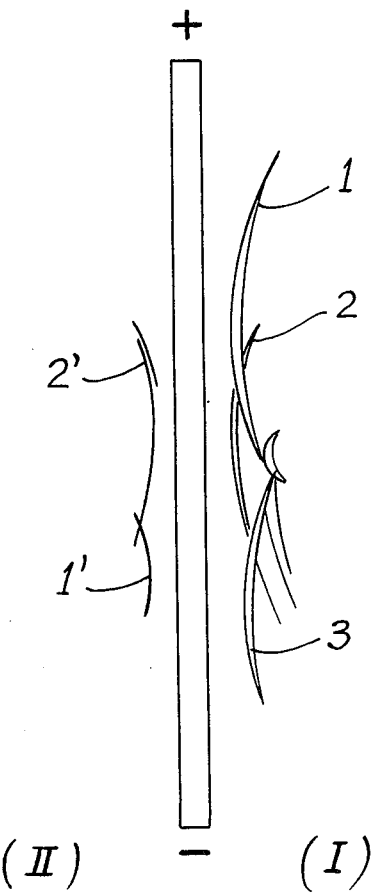

In the immunoelectrophoretic diagram obtained in the same manner with the active fraction according to the invention, and also shown in FIG. 4, two bands subsist, one (2') which corresponds to the postovalbumin and the second (1') which migrates cathodically relative to the first. The active fraction according to the invention thus consists essentially of a postovalbumin and of another protein resembling the ovo-inhibitor.

The pharmacological activity of the ovomucoid fraction according to the invention was studied:

(A) on animals:

Investigation of the anti-histamine action

This investigation was carried out:
on isolated organs (ileum of the rat and of the guinea-pig);
on the arterial pressure and the respiration of a rabbit subjected to the effects of histamine;
on the $LD_{50}$ of histamine in mice.
In the above three sets of experiments, the ovomucoid fraction of quails egg did not exhibit any anti-histamine activity.

On animals (rats, mice, rabbits and guineapigs) treated preventatively for several days with the ovomucoid fraction according to the invention, a varying protective effect on the hypotension and on the histamine-induced bronchospasm was observed.

In contrast, in dogs suffering naturally from an eczema or from a pelada of allergic etiology using a posology of four doses (one dose = 40 $\gamma$ of product in aqueous solution) per day for 9 days, followed by a stoppage for 9 days and then by a resumption of the treatment for 9 days, the observations were a recrudescence of the cutaneous symptoms during the first cure from the 3rd or 6th day, followed by a slight attenuation at the end of the cure, a fresh cutaneous reaction, sometimes major, at the start of the second cure and, towards the end of the latter, a major improvement of the cutaneous symptoms (ranging up to complete disappearance for several months (6 on average) and, in certain cases, several years).

On gradual reappearance of the symptoms, a fresh cure brings about the same initial reaction, followed by a fresh disappearance of the cutaneous symptoms.

In parallel, an improvement in general condition, an awakening of the libido, and humoral changes (lowering of the azotaemia) were observed. High doses (30 doses of 40 $\gamma$ per day for 2 to 3 months) must be reached before diarrhoea symptoms appear.

(B) in man:
Polyallergic asthma was treated orally (6 to 8 doses of 40 $\gamma$ every 4 days) for 1 year.

A progressive attenuation was observed, with the asthma changing to a cough and then to rhinitis with, finally, disappearance of the rhinitis, all these phenomena being very gradual. Stopping the treatment causes the gradual return of the condition, from 4 months to 1 year later.

Following several observations, a posology in accordance with age was studied. The treatment consisted of a first progressive cure of 3 to 7 doses per day for 7 days, followed by a stoppage of 9 days and then followed by a resumption at a dose slightly higher than the first for 9 days, again followed by a stoppage of 9 days and finally by a mini-cure of 6 days at 6 doses per day. In more than 80% of the cases, a recrudescence of the initial condition (or a change from asthma to eczema) was observed between the 3rd and the 6th day, followed by progressive attenuation. The same reaction is observed after the second and even after the third cure. The clinical improvement is thus gradual and only manifests itself about 10 to 15 days after the end of the treatment. It lasts from several months (an average of 4 to 6 months) to several years (5 to 6 years in certain cases).

It is essential that the allergic patient should be in contact with the allergens responsible. In the case of pollinoses, for example, the treatment has no preventative effect whatsoever, and the condition must be treated whilst it is manifesting itself clinically.

On the other hand, even after 8 years of clinical absence, reactions which disappear following a fresh cure can be observed.

As regards the secondary effects, observations made in the course of the cures, in addition to the abovementioned rebound phenomenon, where the appearance of transient headaches, rare cases of digestive intolerance, substantial expectoration and asthenia which is sometimes intense, but short-lived.

The following were also studied in the patients treated:

(a) action on the eosinophils:
The comparison of the number of eosinophils before and after treatment shows substantial changes, with sometimes a marked increase in a short time (3 weeks to 1 month), followed by gradual regularization.

(b) action on the IGE:
A first study of 60 cases, with determination before and after treatment (by radio-immunology and immunodiffusion) shows sometimes substantial changes (a coefficient of 10) in 90% of the cases, in one direction (60% lowering) or the other (30% increase). Thereafter, a long-term normalization (over about 2 years) is assisted.

(c) action on the other humoral constants:

The following were noted; an increase in the number of red blood corpuscles, a reduction in the number of leucocytes, which are numerous initially, little action on the sedimentation rate and little change in the lipid balance; in contrast, a marked lowering of the high uric acid contents was noted initially. In several cases, normalization of of high glycaemia initially, and the disappearance of certain initial glycosurias and albuminurias were noted.

(d) action on the cutaneous tests:

When the patients are subjected to cutaneous tests before and after the initial cure, an exacerbation of these tests is observed in numerous cases, with the negative or doubtful tests becoming positive.

Tests carried out several years after stopping the treatment show a return to the initial tests. In no case do the tests become totally or even partially negative after 10 years of clinical absence.

Therapeutic indication:

The product according to the invention can be used in the treatment of various forms of allergy:

immuno-allergic reactions of type I or allergic illnesses of type I, namely: allergic asthma, non-seasonal allergic rhinitis (and laryngitis), pollinosis (with rhinitis, conjunctivitis and sometimes asthma), acute urticaria, prevention of anaphylactic shock (penicillin, or stings of hymenoptera), and certain digestive disturbances (Quincke oedema and vomiting), allergies of type II (inhibition of fixation of the complement) and allergies of types III and IV (eczema).

It can also be administered equally successfully in cases of hepatic disturbances (after effects of hepatitis, or cirrhosis) in the case of pancreatites and in the case of α-1 anti-trypsin deficiencies.

The original nature of the treatment by the product according to the invention obviously has a bearing on several points:

(1) The need for the presence of the hostile antigens in order that the treatment shall be effective. For example, in the case of a polyallergic asthma, ensuring the absence of feathers during the treatment causes only an incomplete result because the allergy to feathers persists; in the case of an allergy to feathers, dust and pollens, an effective treatment is only possible at the pollen season or requires a repeat cure in that season;

(2) semi-rapid action: the therapeutic result is only achieved after three weeks or one month, but lasts for 6 months to several years;

(3) modification of the terrain: this manifests itself by the action on the IGE and by the skin tests, on the one hand, and, on the other hand, by the change in the clinical signs of the allergy during this therapy (gradual improvement, conversion of the asthma to cough and then to rhinitis, or of the asthma to eczema, or vice versa);

(4) no definitive cure: the treatment requires fresh supplies of the product according to the invention, but only at the time when a relapse takes place;

(5) no direct anti-histamine action either in man or in animals;

(6) no preventative action, compared to that which takes place in the case of desensitization by means of corticoids or by means of allergo-globulins.

As regards the mode of action of the medicament according to the invention, it is two-fold, namely:

an atopical antigen action, causing, in the first stage, an antigen-antibody conflict, followed by a blockage/inhibition of the pre-existing antibodies (a tachyphylaxis effect), and an anti-protease action, in particular an anti-(human trypsin) action.

It furthermore would appear that the ovomucoid according to the invention makes it possible to make good a pre-existing deficit, which can only be an immunitary deficit.

On this hypothesis, especially in the case of bronchial asthma, the medicament would simply supplement the human phenotypes deficient in α-1 anti-trypsin and reestablish the level of inhibition required to cancel out the action of the elastase liberated by the granulocyte.

We claim:

1. An ovomucoid fraction of the white of quails eggs, which exhibits an anti-cattle-trypsin-activity of the order of 100 units per mg and consists essentially of a postovalbumin and of a protein corresponding to protein Y, according to the proteinogram obtained by electrophoresis on starch gel.

2. As a medicament, useful in the treatment of allergies comprising an effective amount of the active fraction of claim 1 in a carrier for adminstration.

3. A process for the preparation of the ovomucoid fraction of the white of quails eggs as claimed in claim 1, characterized in that it comprises the following stages:

after adding to the white of egg one volume of a solution of trichloroacetic acid in acetone, containing 1 volume of 0.5 M trichloroacetic acid per 2 volumes of acetone, the mixture is allowed to settle at 4° C. and after 48 hours the clear supernatant liquid is separated off, the anti-protease fraction is precipitated by adding from 2 to 3 volumes of acetone to the supernatant liquid and the precipitate is filtered off; and the precipitate is dissolved in water and dialyzed to remove the excess trichloroacetic acid, after which it is reprecipitated with acetone, washed with acetone and ether and dried at ambient temperature.

4. A process as claimed in claim 3, in which the starting material used is the white of the eggs of the quail Coturnix coturnix japonica.

* * * * *